US012109187B2

(12) United States Patent
Horzempa et al.

(10) Patent No.: US 12,109,187 B2
(45) Date of Patent: Oct. 8, 2024

(54) ANTIMICROBIAL COMPOSITIONS AND RELATED METHODS

(71) Applicants: WEST LIBERTY UNIVERSITY, West Liberty, WV (US); UNIVERSITY OF MISSISSIPPI, University, MS (US)

(72) Inventors: Joseph A. Horzempa, Pittsburgh, PA (US); Elliot M. Collins, Crooksville, OH (US); Juan Francisco Leon, Gainesville, FL (US)

(73) Assignees: West Liberty University, West Liberty, WV (US); University of Mississippi, University, MS (US)

(*) Notice: Subject to any disclaimer, the term of this patent is extended or adjusted under 35 U.S.C. 154(b) by 76 days.

(21) Appl. No.: 17/396,223

(22) Filed: Aug. 6, 2021

(65) Prior Publication Data

US 2022/0040146 A1 Feb. 10, 2022

Related U.S. Application Data

(60) Provisional application No. 63/062,767, filed on Aug. 7, 2020.

(51) Int. Cl.
*A61K 31/36* (2006.01)
*A61K 31/09* (2006.01)
*A61P 31/04* (2006.01)

(52) U.S. Cl.
CPC .............. *A61K 31/36* (2013.01); *A61K 31/09* (2013.01); *A61P 31/04* (2018.01)

(58) Field of Classification Search

CPC ...................................................... A61K 31/36
See application file for complete search history.

(56) References Cited

U.S. PATENT DOCUMENTS

| | | | |
|---|---|---|---|
| 4,876,277 | A | 10/1989 | Burke et al. |
| 2010/0048573 | A1 | 2/2010 | Sperandio et al. |

OTHER PUBLICATIONS

United States Patent and Trademark Office, International Search Report and Written Opinion issued in corresponding Application No. PCT/US2021/045003, mailed Dec. 27, 2021.
Pubchem SID 293113463, Available Date: Jan. 20, 2016 (retrieved on Nov. 24, 2021), Retrieved from https://pubchem.ncbi.nlm.nih.gov/substance/293113463.
Ferreira, R.G., et al. "Antifungal Action of the Dillapiole-rich Oil of Piper aduncum against Dermatomycoses Caused by Filamentous Fungi," BJMMR, 15(12): 1-10, 2016; Article No. BJMMR 26340.
Parise-Filho, R., et al. "The anti-inflammatory activity of dillapiole and some semisynthetic analogues," Pharmaceutical Biology, 2011; 49(11): 1173-1179.
Brazao, M.A.B.,, et al. "Antibacterial activity of the Piper aduncum oil and dillapiole, its main constituent, against multidrug-resistant strains," Boletin Latinoamericano y del Caribe de Plantas Medicinales y Aromaticas, vol. 13, No. 6, 2014, pp. 517-526.

*Primary Examiner* — Paul V Ward
(74) *Attorney, Agent, or Firm* — Stites & Harbison, PLLC; Terry L. Wright

(57) ABSTRACT

A pharmaceutical composition is provided that comprises an effective amount of dillapiole or a derivative thereof, and a pharmaceutically-acceptable vehicle, carrier, or excipient. Methods of treating a bacterial infection are also described and include administering an effective amount of dillapiole or a derivative thereof to a subject in need of such treatment. Methods of reducing bacterial virulence are further described and include contacting a bacterium, such as a *F. tularensis* or *A. baumannii* bacterium, with an effective amount of dillapiole or a derivative thereof.

11 Claims, 6 Drawing Sheets

ANTIMICROBIAL COMPOSITIONS AND RELATED METHODS

RELATED APPLICATIONS

This application claims priority from U.S. Provisional Application Ser. No. 63/062,767, filed Aug. 7, 2020, the entire disclosure of which is incorporated herein by this reference.

GOVERNMENT INTEREST

This invention was made with government support under grant numbers 2P20GM103434-16, 2P20GM103434-17, 2P20GM103434-18, and 2P20GM103434-19 awarded by the National Institutes of Health. The government has certain rights in the invention.

TECHNICAL FIELD

The presently-disclosed subject matter generally relates to antimicrobial compositions and related methods. In particular, certain embodiments of the presently-disclosed subject matter relate to antimicrobial compositions comprising dillapiole or derivatives thereof, and methods of using those compositions for the treatment of bacterial infections, including bacterial infections arising from *F. tularensis* and *A. baumannii* bacteria.

BACKGROUND

According to the Center for Disease Control and Prevention, there have been more than 2 million people infected with drug-resistant bacteria in the United States, resulting directly in over 23,000 deaths in the past year. Almost as quickly as scientists discover and develop new small molecule antibiotic compounds that target the biosynthetic machinery of bacteria, these pathogens acquire resistance. Thus, current treatment strategies rely upon a continuous need for novel antibiotics.

Of particular interest in the identification of compounds that target drug-resistant bacteria is the identification of compounds that target *Francisella tularensis*, a category A bioterror agent whose intentional release could be disastrous. *F. tularensis* causes the disease tularemia. One of the most well-studied interactions between *F. tularensis* and its host involves the ability of this bacterium to replicate within macrophages and monocytes—immune cells that typically phagocytose and kill bacteria. The ability to replicate within these host cells is required for the pathogenesis of *F. tularensis* (J Bacteriol. 2004 October; 186(19):6430-6). Therefore, many investigators have tested mutant strains for their ability to replicate in macrophages in vitro as a surrogate or correlate for in vivo pathogenesis as these two phenomena are usually consistent (Infect Immun. 2010 June; 78(6):2607-19; J Bacteriol. 2004 October; 186(19): 6430-6).

Despite the efforts of investigators, a vaccine against tularemia that is licensed for human use still does not exist, thus leaving humans vulnerable to this pathogen. Current treatments for tularemia do exist as, for example, doxycycline, gentamicin, and ciprofloxacin have all been used clinically to treat tularemia patients. However, those antibiotics are each traditional small molecule antibiotics for which resistance can be developed. In addition, it is appreciated that weaponized *F. tularensis* can be engineered to be resistant to all known antibiotics used, thereby rendering individuals clinically vulnerable. There is no current solution to this problem. Accordingly, antimicrobial compositions and therapies capable of filling this unmet need and that can be added to strategic antibiotic stockpiles that are used in emergency situations would be both highly desirable and beneficial.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes antimicrobial compositions and related methods. In particular, certain embodiments of the presently-disclosed subject matter include antimicrobial compositions comprising dillapiole or derivatives thereof, and methods of using those compositions for the treatment of bacterial infections, including bacterial infections arising from *F. tularensis* and *A. baumannii* bacteria.

In some embodiments of the presently-disclosed subject matter, a pharmaceutical composition is provided that comprises an effective amount of dillapiole or a derivative thereof, and a pharmaceutically-acceptable vehicle, carrier, or excipient. In some embodiments, the pharmaceutical composition comprises dillapiole. In other embodiments, the pharmaceutical composition includes a dillapiole derivative.

In some embodiments, the pharmaceutical composition comprises a dillapiole derivative having the formula:

where $R_1$ and $R_2$ in the above formula are independently selected from a hydrogen atom and an alkyl group. For instance, in some embodiments, a pharmaceutical composition is provided where the dillapiole derivative is selected from the group consisting of:

In other embodiments of the presently-disclosed subject matter, a pharmaceutical composition is provided that comprises a dillapiole derivative having the formula:

where $R_1$ in the above formula is a propene group, a propyne group, a propane group, an isopropyl group, or a cyclopropyl group.

In further embodiments, a pharmaceutical composition is provided where the pharmaceutical composition comprises a dillapiole derivative having the formula:

with $R_1$ and $R_2$ in the above formula being independent from one another and being either a branched or unbranched alkyl group having 1 to 6 carbon atoms.

In some embodiments of the pharmaceutical compositions described herein, the dillapiole or the derivative thereof is included in the composition in an amount sufficient to reduce an expression of one or more virulence factors in a bacterium, to reduce the activity of MglA/SspA in the bacterium, or to reduce replication of the bacterium.

Further provided, in some implementations of the presently-disclosed subject matter, are methods for treating a bacterial infection. In some implementations, a method for treating a bacterial infection is provided that comprises administering to a subject in need thereof an effective amount of the dillapiole and/or one or more of the derivatives thereof described herein. In some implementations of the therapeutic methods, administering the dillapiole comprises administering an amount of dillapiole sufficient to reduce an amount of expression of one or more virulence factors in a bacterium, to reduce an amount of activity of MglA/SspA in the bacterium, or to reduce an amount of replication by the bacterium. In some implementations, the replication is intracellular replication, such as intracellular replication of the bacterium inside the cell of a host. Moreover, such bacteria capable of being treated with the presently-disclosed therapeutic methods can, in certain implementations include antibiotic resistant bacteria. In some implementations, the bacterium is *F. tularensis* or *A. baumannii*. In some implementations, by administering the dillapiole and/or one or more of the derivatives thereof, an expression level of tumor necrosis factor alpha (TNFα) is reduced in the subject.

Still further provided, in some implementations of the presently-disclosed subject matter are methods for reducing bacterial virulence. In some implementations, a method for reducing bacterial virulence is provided that comprises contacting a bacterium with an effective amount of dillapiole and/or a derivative thereof. In some implementations, contacting the bacterium comprises contacting the bacterium with an amount of the dillapiole or a derivative thereof sufficient to reduce an amount of activity of MglA/SspA in the bacterium or to reduce an expression level of one or more genes controlled by MglA/SspA in the bacterium. In some implementations, the one or more genes are encoded by the *Francisella* pathogenicity island (FPI). In some implementations, the bacterium is an antibiotic resistant bacterium and/or is a bacterium selected from *F. tularensis* or *A. baumannii*.

Further features and advantages of the present invention will become evident to those of ordinary skill in the art after a study of the description, figures, and non-limiting examples in this document.

BRIEF DESCRIPTION OF THE DRAWINGS

FIG. 4B shows THP-1 cells infected with *F. tularensis* LVS, treated with gentamicin at 2 h post infection, washed, and then treated with the indicated concentration of dillapiole (data represent mean CFU±SD).

DESCRIPTION OF EXEMPLARY EMBODIMENTS

Figure 1:
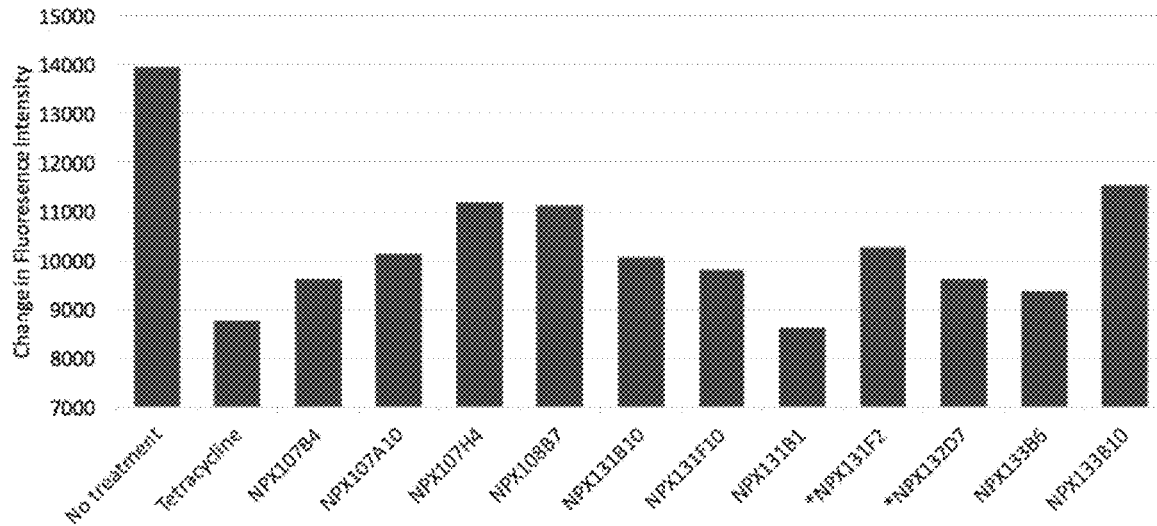
FIG. 1 includes a graph and table showing plant extracts that inhibit intracellular growth of *F. tularensis*, where 58 extracts that inhibited growth of *F. tularensis* in THP-1 cells (a human monocyte line, not shown) were initially identified and, of those, eleven compounds were identified that could act as immunomodulators as those compounds inhibited bacterial growth during infection of THP-1 cells but not in disk diffusion assays (not shown; * indicates extracts that may exhibit both immunomodulatory and direct antibacterial activity), where the top panel shows intracellular growth that was measured by the change in fluorescence over 48 hours (bacteria were red fluorescent *F. tularensis* Live Vaccine Strain (LVS)/pTC3D) and with infected cells treated with tetracycline serving as a positive control for inhibition, and where the bottom panel includes a table listing the genus/species, family, and common names of the sources of these compounds that exhibited inhibition of intracellular *F. tularensis* infection through immunomodulation or a reduction of pathogenesis.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

The present application can "comprise" (open ended), "consist of" (closed ended), or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is based, at least in part, on the identification of an antimicrobial therapy comprising dillapiole and/or derivatives thereof and that exhibits a novel mechanism of action. In particular, it has been observed that when exposed to the compound, dillapiole, *Francisella tularensis* bacteria dampen expression of many virulence-associated genes, including genes encoded by the *Francisella* pathogenicity island (FPI) and which are required for pathogenesis. In some embodiments, and without wishing to be bound by any particular theory or mechanism, such dampening of virulence factor expression is believed to be due to the targeting of the transcriptional activators, MglA and/or SspA, as transcription of the MglA/SspA regulon is diminished in bacteria treated with dillapiole. Treatment of infected mammalian host cells with dillapiole also results in a substantial decrease in bacterial viability. The presently-disclosed subject matter thus includes antimicrobial compositions comprising dillapiole and/or derivatives thereof, as well as methods of using those compositions for the treatment of bacterial infections, including bacterial infections arising from antibiotic-resistant strains of *F. tularensis*.

In some embodiments of the presently-disclosed subject matter, a pharmaceutical composition is provided that comprises an effective amount of dillapiole or a derivative thereof, and a pharmaceutically-acceptable vehicle, carrier, or excipient. In some embodiments, the pharmaceutical composition comprises dillapiole, one or more derivatives of dillapiole, or combinations thereof. In some embodiments, the dillapiole included in the presently-described compositions and used in accordance with the presently-disclosed subject matter has the chemical structure as shown below and in FIG. 3.

Dillapiole

As noted above, in other embodiments, the dillapiole is a derivative of the dillapiole having the foregoing chemical structure. In some embodiments, a derivative of dillapiole is provided and utilized in which the dioxolane ring is opened as shown in the chemical structure provided below as general formula (I):

(I)

where $R_1$ and $R_2$ are independently selected from a hydrogen atom and an alkyl group. As used herein the term "alkyl" refers to C1-20 inclusive, linear (i.e., "straight-chain" or "unbranched"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, methylpropynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a C1-8 alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms.

In some embodiments of the dillapiole derivatives of general formula (I) shown above, $R_1$ is independently selected from a hydrogen atom or a methyl group and $R_2$ is also independently selected from a hydrogen atom or a methyl group. For example, in some embodiments, a dillapiole derivative of general formula (I) is selected from the following compounds:

and

In other embodiments, a derivative of dillapiole is provided and utilized having the general formula (II) below:

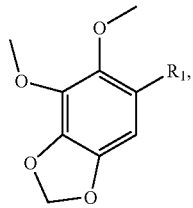

(II)

where $R_1$ is selected from a propene group, a propyne group, a propane group, an isopropyl group, or a cyclopropyl group. For example, in some embodiments, a derivative of dillapiole of the general formula (II) is provided and utilized in which propenyl group of the dillapiole is modified to include an alternative double bond, a triple bond, or a cyclopropyl group keeping the 3 carbon atoms, but changing the alkyl chain carbon hybridization from sp2 to sp3 or sp, as shown below.

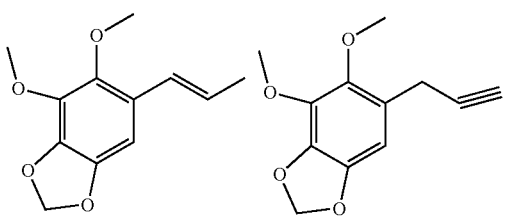

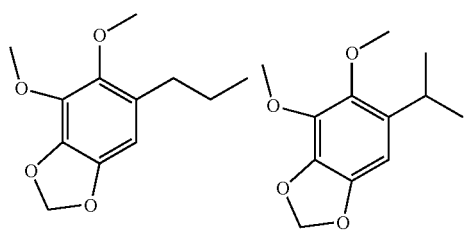

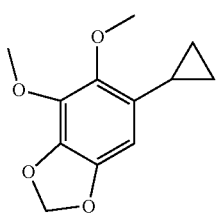

In further embodiments, a derivative of dillapiole is provided and utilized in which one or more additional substituent groups are added to the parent dillapiole structure shown above and in FIG. 3. In some such embodiments, a dillapiole derivative is provided having the general formula (III) below:

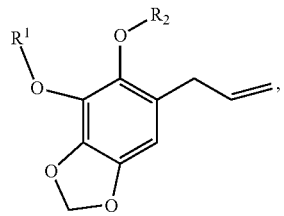

(III)

where $R_1$ and $R_2$ are independent from one another and are a branched or unbranched alkyl group having 1 to 6 carbon atoms. As an example, in some embodiments, a derivative of dillapiole of general formula (III) is provided having the structures below, where either $R_1$ or $R_2$ are a methyl group while the other of $R_1$ or $R_2$ is an alkyl group selected from ethyl, propyl, isopropyl, butyl, secbutyl, and the like.

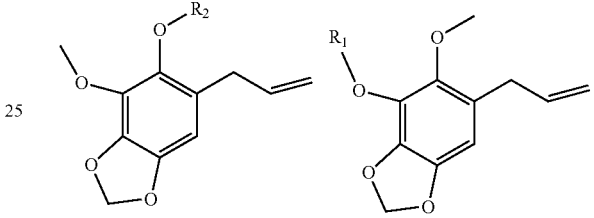

In some embodiments of the compositions described herein, to produce a dillapiole derivative of the presently-disclosed subject matter, a high concentration of dillapiole is first obtained by isolating dillapiole from certain plant species, for example, from the leaves of different Piper species (see, e.g., Pharm. Biol. 2011, 49(11), 1173-1179). In other embodiments, rather than isolating dillapiole, dillapiole can alternatively be synthesized through several methods, such as through the use of sesamol (a common monolignan) as a starting material (see, e.g., Can J. Chem. 2000, 78, 1345-1355). Briefly, sesamol can be converted to the ortho alkylated phenol by a Claisen rearrangement, followed by introduction of the formyl group through the use of formaldehyde, tin tetrachloride and tributylamine to obtain the aldehyde derivative. Subsequently, the phenol group can be methylated and the aldehyde hydrolyzed using meta chloroperoxybenzoic acid to obtain the hydroxyl group and the methylation of the phenol to yield dillapiole.

Once dillapiole is isolated or synthesized, and as one example of a means of synthesizing a dillapiole derivative of the presently-disclosed subject matter, different semisynthetic methods based on protection and deprotection can then applied to prepare different alkyl groups at the two different methyl ether linkages $R_1$ and $R_2$ shown in general formula (III) above using standard protection/deprotection procedures (see, e.g., Wuts, P. G. M.; Greene, T. W. in Greene's protective groups in organic synthesis, $4^{th}$ edition, John Wiley and Sons, Inc., 2007). In other embodiments, and as a further example of a dillapiole derivative synthesis procedure, the terminal double bond at the alkyl chain in dillapiole can be hydrogenated using a reductor, such as, for example, sodium borohydride, to semi-synthesize dihydrodillapiole, in the same sense the isomerization of the double bond can be achieved through basic conditions, for example potassium hydroxide on butanol to yield the isodillapiole. Using such reaction conditions, the dillapiole derivatives of general formula (II) can be produced. In a similar manner, in some embodiments, opening of the dioxolane ring can be achieved by previous protection of the ether substituents and action of boron tribromide (see, e.g., Journal of the Chemical Society, Perkin Transactions 1: 1981, 7, 1807-1810) following a general procedure of protection/deprotection of the methyl ether groups before the ring opening. By making use of the above-described procedures, however, the dillapiole derivatives of the presently-disclosed subject matter can be produced having biological activities comparable to or exceeding those observed with the parent compound as such derivative compounds generally have greater than or equal to 85% similarity to the active parent dillapiole compound (see, e.g., ref. J. Med. Chem. 2002, 45, 4350-4358), further allowing each of the dillapiole derivatives described herein to then be effectively incorporated into a pharmaceutical composition.

The term "pharmaceutically-acceptable carrier" as used herein refers to sterile aqueous or nonaqueous solutions, dispersions, suspensions, or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants, such as preservatives, wetting agents, emulsifying agents and dispersing agents. Further prevention of the action of microorganisms can be ensured by the inclusion of various other antibacterial and antifungal agents such as paraben, chlorobutanol, phenol, sorbic acid and the like. It can also be desirable to include isotonic agents such as sugars, sodium chloride and the like.

Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of compound to biodegradable polymer and the nature of the particular biodegradable polymer employed, the rate of compound release can be controlled. Depot injectable formulations can also be prepared by entrapping the compound in liposomes or microemulsions, which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations can further include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents.

The compositions can also take forms such as suspensions, solutions, or emulsions in oily or aqueous vehicles, and can contain formulatory agents such as suspending, stabilizing and/or dispersing agents. Alternatively, the compounds can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically-acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration, the compositions can take the form of tablets or lozenges formulated in a conventional manner.

The compositions can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). The compounds can also be formulated in rectal compositions, creams or lotions, or transdermal patches.

In some embodiments, and as described in further detail below, the dillapiole and/or the derivative thereof is included in the composition in an amount sufficient to: reduce an expression of one or more virulence factors in a bacterium; reduce the activity of MglA/SspA; and/or reduce an amount of replication of a bacterium. In some embodiments, the bacterium is an antibiotic-resistant bacterium. In some embodiments, the bacterium is selected from *F. tularensis* or *A. baumannii*.

Further provided, in some embodiments of the presently-disclosed subject matter, are methods for treating a bacterial infection. In some embodiments, a method for treating a bacterial infection is provided that comprises administering to a subject in need thereof an effective amount of dillapiole and/or a derivative thereof. The terms "treatment" or "treating" are used herein to refer to the medical management of a subject with the intent to cure, ameliorate, stabilize, or prevent a bacterial infection. This term includes active treatment, that is, treatment directed specifically toward the improvement of a bacterial infection, and also includes causal treatment, that is, treatment directed toward removal of the cause of the bacterial infection. In addition, this term includes: palliative treatment, or treatment designed for the relief of symptoms rather than the curing of the bacterial infection; preventative treatment, or treatment directed to minimizing or partially or completely inhibiting the development of the bacterial infection; and supportive treatment, or treatment employed to supplement another therapy directed toward the improvement of the associated bacterial infection.

For administration of a therapeutic composition as disclosed herein (e.g., a composition comprising an effective amount of dillapiole and/or a derivative thereof), conventional methods of extrapolating human dosage based on doses administered to a murine animal model can be carried out using the conversion factor for converting the mouse dosage to human dosage: Dose Human per kg=Dose Mouse per kg/12 (Freireich, et al., (1966) Cancer Chemother Rep. 50: 219-244). Doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate kg factor. In an adult human, 100 mg/kg is equivalent to 100 mg/kg×37 kg/sq m=3700 mg/m$^2$.

Suitable methods for administering a therapeutic composition in accordance with the methods of the presently-disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, dermally (e.g., topical application), intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082). In some embodiments of the therapeutic methods described herein, the therapeutic compositions are administered intravenously or orally to treat a bacterial infection.

Regardless of the route of administration, the therapeutic agents used in accordance with the presently-disclosed subject matter are typically administered in an amount effective to achieve the desired response. As such, the term "effective amount" is used herein to refer to an amount of the therapeutic composition sufficient to produce a measurable biological response (e.g., a decrease in bacterial replication or a reduction in the expression of bacterial virulence factors). Actual dosage levels of active ingredients in a therapeutic composition used in accordance with the presently-disclosed subject matter can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, New Jersey; Goodman et al., (1996) Goodman & Gilman's the Pharmacological Basis of Therapeutics, 9th ed. McGraw-Hill Health Professions Division, New York; Ebadi, (1998) CRC Desk Reference of Clinical Pharmacology. CRC Press, Boca Raton, Florida; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pennsylvania; and Speight et al., (1997) Avery's Drug Treatment: A Guide to the Properties, Choice, Therapeutic Use and Economic Value of Drugs in Disease Management, 4th ed. Adis International, Auckland/Philadelphia; Duch et al., (1998) *Toxicol. Lett.* 100-101:255-263.

In some embodiments, administration of the dillapiole in accordance with the presently-disclosed subject matter affects one or more of the underlying mechanisms of action or causes of the bacterial infection such that the pharmaceutical compositions and methods described herein can be used with a minimal risk that antibiotic resistance will develop in the bacteria being treated. For example, in some embodiments, administering the dillapiole reduces an expression level of tumor necrosis factor alpha (TNFα). As another example, in some embodiments, administering the dillapiole reduces an amount of expression of one or more virulence factors in or by a bacterium.

The term "virulence factor" is used herein to refer to molecules, such as polypeptides, that are produced by bacteria, as well as viruses, fungi, and protozoa, and which enable those organisms to achieve certain functions including, but not limited to, the ability of those organisms to achieve colonization in a particular host such as by attachment to the cells of the host, to evade or inhibit a host's immune response, to gain entry into and exit from the cells of the host, and/or to obtain nutrition from the host. Such virulence factors can vary widely depending on the particular organism and each particular organism can include a wide array of virulence factors from a variety of different sources. In bacteria, for example, such virulence factors can include factors that assist and promote colonization of the host, such as adhesins, invasins, and antiphagocytic factors, as well as factors that damage the host, either directly or indirectly, such as toxins, hemolysins, and proteases. Such virulence factors can be chromosomally encoded and intrinsic to the bacteria (e.g., capsules and endotoxin), while other virulence factors in bacteria can be obtained from mobile genetic elements like plasmids and bacteriophages (e.g., some exotoxins).

In some embodiments, reducing the amount of virulence factors in or by a bacterium is achieved by modulating a transcriptional activator required for pathogenesis of the bacterium. For instance, in some embodiments, the dillapiole reduces an amount of activity of the transcription factors MglA and SspA in a bacterium, which are transcription factors that are known to form a heterodimer complex and interact with RNA polymerase to regulate the expression of the pathogenic genes in certain bacteria. In some embodiments, administration of dillapiole reduces an amount of replication by a bacterium itself, such as, in certain embodiments, an amount of intracellular replication as may occur during *F. tularensis* replication in macrophages (see, e.g., Mol Cell. 2021 Jan. 7; 81(1):139-152.e10).

Still further provided, in some embodiments of the presently-disclosed subject matter, are methods for reducing bacterial virulence that comprise a step of contacting a bacterium with an effective amount of dillapiole and/or a derivative thereof. In some embodiments, contacting the bacterium with the dillapiole and/or the derivative thereof reduces an amount of activity of MglA/SspA in the bacterium. In some embodiments, contacting the bacterium with the dillapiole reduces an expression level of one or more genes controlled by MglA/SspA, such as, in certain embodiments, one or more genes encoded by the *Francisella* pathogenicity island (FPI), a cluster of 15-20 genes generally regarded as important for the growth and virulence of *F. tularensis* (see, e.g., Front. Cell. Infect. Microbiol., 23 Apr. 2018).

With respect to the bacterial infections and bacterium treated in accordance with the presently-disclosed subject matter or otherwise contacted with an effective amount of dillapiole, in some embodiments, the bacterium responsible for the bacterial infection is an antibiotic resistant bacterium. In some embodiments, the bacterium is selected from *F. tularensis* or *A. baumannii*. In some embodiments, the bacterium is a bacterium that relies on the activity of MglA/SspA for pathogenesis.

Various methods known to those of ordinary skill in the art can be used to determine virulence factor as well as other protein (e.g., MglA/SspA) expression level or activity in a bacterium as well as an amount of bacterial replication. For example, in some embodiments, a gentamicin protection assay can be used to measure an amount of intracellular bacterial replication. Of course, determination of protein or nucleic acid expression levels can be made by any number of methods known to those skilled in the art including, but not limited to, of ELISA, Luminex, FACs, Western blot, dot blot, immunoprecipitation, immunohistochemistry, immunocytochemistry, immunofluorescence, immunodetection methods, optical spectroscopy, radioimmunoassay, mass spectrometry, HPLC, qPCR, RT-qPCR, multiplex qPCR, SAGE, RNA-seq, microarray analysis, FISH, MassARRAY technique, and combinations thereof.

With respect to the reduction in virulence factor expression levels, the reduction in the activity of MglA/SspA, the reduction in bacterial replication, or similar reductions, the terms "reversal" or "inhibition" or "decrease" or "dampen" or "reduction" do not necessarily refer to the ability to completely reverse or completely inactivate all target biological activity in all cases. Rather, the skilled artisan will understand that the term "inhibiting" as well as the term "reversal" or "reduce" refers to decreasing biological activity or inactivity of a target. Such decreases in biological activity or inactivity can be determined relative to a control, wherein the control can be representative of an environment in which a therapeutic agent is not administered. For example, in some embodiments, a decrease in activity or inactivity relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

With still further regard to the various methods described herein, although certain embodiments of the methods disclosed herein only call for a qualitative assessment, other embodiments of the methods call for a quantitative assessment. Such quantitative assessments can be made, for example, using known methods, as will be understood by those skilled in the art.

The skilled artisan will also understand that measuring a reduction in virulence factors, replication, or change in other activity or expression levels is a statistical analysis. For example, a reduction in expression can be compared to a control level of expression (e.g., a level of expression observed in bacteria not treated with dillapiole), and an amount of virulence factor or other protein expression of less than or equal to the control level can be indicative of a reduction in the expression, as evidenced by a level of statistical significance. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

As used herein, the term "subject" includes both human and animal subjects. Thus, veterinary therapeutic uses are provided in accordance with the presently disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Figure 2:
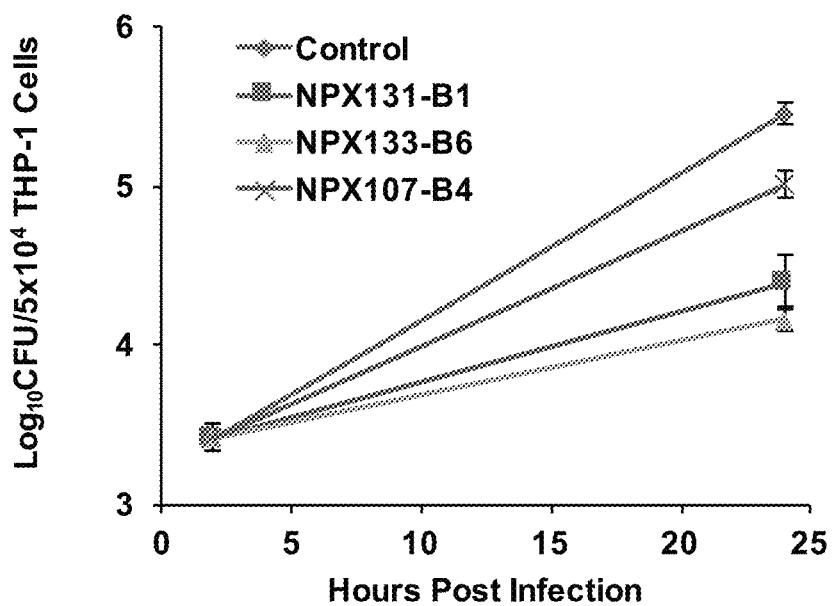
FIG. 2 is a graph showing that human monocyte cells treated with plant extracts limit intracellular replication of *F. tularensis*, where human THP-1 monocytes were infected with *F. tularensis* LVS, and were subjected to a gentamicin protection assay, and where at two hours post infection, cells were treated with the extract indicated (NPX131-B1, Fennel, Hinojo; NPX133-B6 Hercule's club; NPX107-B4 Willow herb; data represent mean colony forming units (CFU)±SD).
Figure 3:
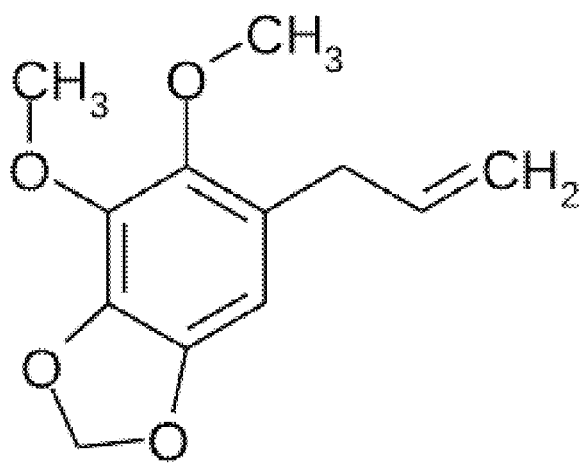
FIG. 3 shows the structure of the active compound (dillapiole) isolated from *Foeniculum vulgare*.
Figure 4A:
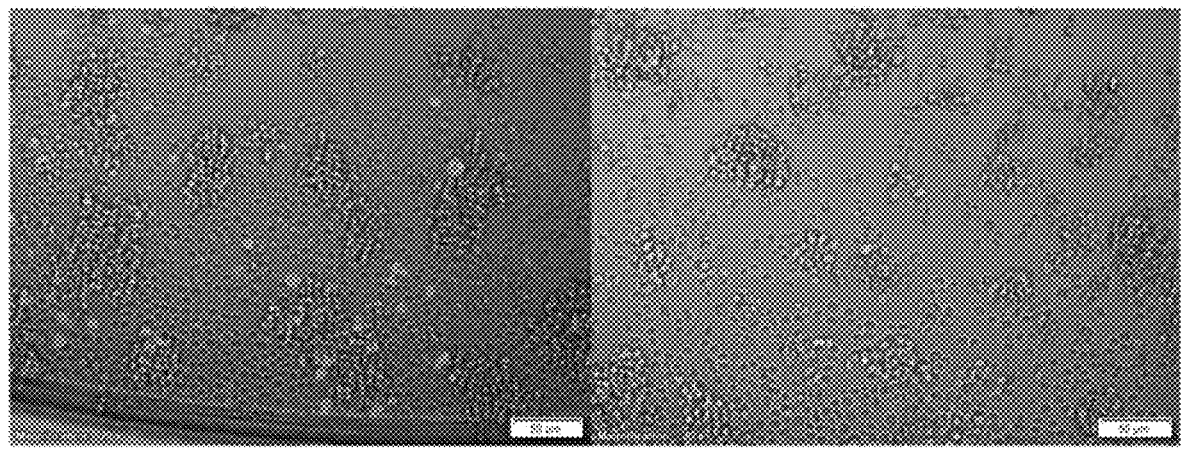
FIGS. 4A-4B includes images and a graph showing dillapiole inhibits replication of *F. tularensis* in human THP-1 monocytes, where FIG. 4A, left panel, shows untreated control brightfield and red fluorescence overlay with red spots indicating cells infected with LVS/pTC3, where FIG. 4A, right panel, shows a treated group brightfield and red fluorescence overlay with the images captured 48 h post infection and with similar exposure time to image in the left panel, and where
Figure 4B:
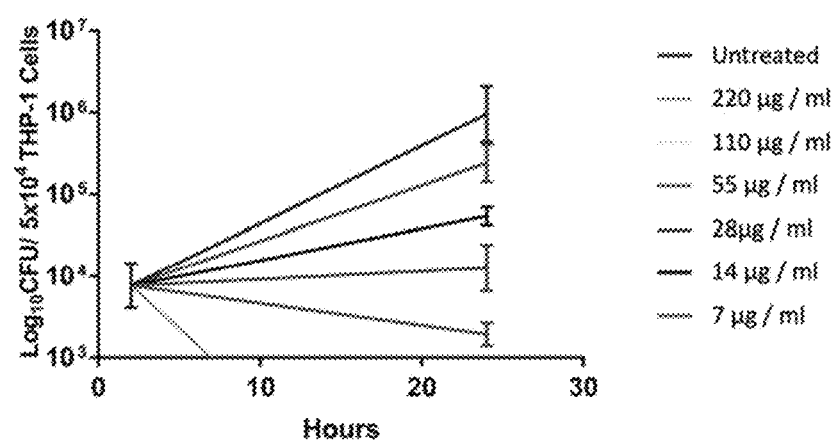
Figure 5:
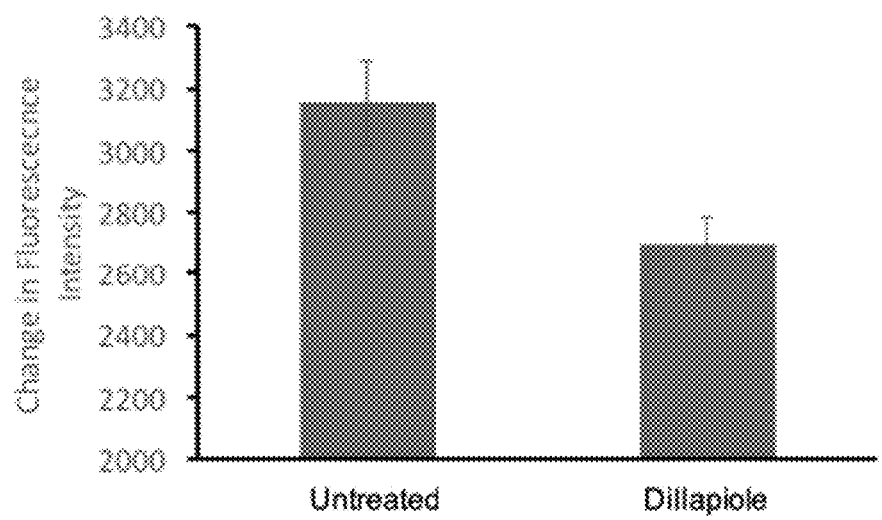
FIG. 5 is a graph showing dillapiole inhibits replication of *F. tularensis* in RAW 264.7 mouse macrophages, where RAW 264.7 cells were infected with LVS/pTC3D (a red fluorescent strain) and were then left untreated or were treated with dillapiole, and where differences in fluorescence intensity over a 48 h infection were measured (mean change in fluorescence±SEM shown).

A compound library that contained extracts of plants, fungi, marine, and algal species (approximately 3000 extracts) was screened. It was observed that extracts from 11 different products from the library were capable of limiting replication of *F. tularensis* in the presence of human monocytes (THP-1 cells) (FIG. 1). Interestingly, these extracts had no effect on bacterial growth during bacterial cultivation in rich growth media (data not shown). This indicated that either the compounds were augmenting host immune responses or diminished bacterial virulence factor expression. First, to validate the screen, a gentamicin protection assay was performed (an in vitro infection model designed to enumerate intracellular bacteria). Here THP-1 cells were infected with *F. tularensis* live vaccine strain (LVS). After a two-hour incubation at 37° C., 5% $CO_2$, cells were treated with gentamicin to kill extracellular bacteria. After washing to remove gentamicin and dead bacteria, cells were treated with a extract product, and bacterial colony forming units (CFUs) were determined at 2 and 24 h post infection (FIG. 2). As expected, all extracts tested via gentamicin protection assay significantly diminished the intracellular replication of *F. tularensis* LVS (FIG. 2). Through bio-assay guided fractionation, the active immunostimulatory compound was then purified and identified from *Foeniculum vulgare* (Fennel, Hinojo) which was determined to be dillapiole (FIG. 3). This pure compound alone (both the purified version and bona fide dillapiole purchased from Sigma Aldrich) was sufficient to inhibit replication of *F. tularensis* during infection of both human THP-1 monocytes (FIGS. 4A-4B) and RAW 264.7 mouse macrophages (FIG. 5). Through the use of gentamicin protection assays to evaluate infection of THP-1 cells, it was determined that the minimum inhibitory concentration (MIC) for dillapiole was less than 7 µg/ml (FIG. 4B), indicating that the potency of this compound can allow for therapeutic use. Microscopic inspection indicated that the dillapiole compound is not toxic to mammalian cells (data not shown) validating that the inhibition of replication of *F. tularensis* was either due to an inflammatory response or downregulation of bacterial virulence.

To investigate whether augmentation of the immune response was responsible for the decreased bacterial viability in host cells treated with dillapiole, the expression of over 20 proinflammatory cytokines was analyzed using the Bio-Rad BioPlex system. The only cytokine that was significantly affected by dillapiole treatment was TNFα (dillapiole treatment decreased TNFα production; confirmed by ELISA; data not shown). RNA-seq of THP-1 cells treated with dillapiole did not reveal substantial alteration of expression of a major immunological or physiological pathway involved in controlling intracellular replication (data not shown). Therefore, the cytokine and RNA-seq data of mammalian cells treated with dillapiole do not reveal an obvious host mechanism that could explain the reduction of intracellular bacteria.

Bacteria treated with dillapiole, however, did show a decrease in expression of several key virulence factors (including genes encoded by the FPI) (Table 1). In fact, the MglA/SspA regulon was affected by dillapiole treatment (Table 1). Because both of those transcriptional activators are required for pathogenesis and intracellular replication of *Francisella tularensis* (Mol Microbiol. 1998 July; 29(1): 247-59; Infect Immun. 2006 December; 74(12):6642-55; PLoS Pathog. 2007 June; 3(6):e84), it was concluded that dillapiole attenuates the pathogenesis of *F. tularensis* by inhibiting the activity of MglA/SspA.

TABLE 1

*Francisella tularensis* LVS genes controlled by MglA/SspA that exhibit significantly decreased expression following treatment with dillapiole. FPI genes are in italics. Genes controlled by SspA are marked with ***.

| Locus tag | Gene name |
|---|---|
| FTL_0881 | hypothetical protein |
| FTL_0026 | 3-hydroxyisobutyrate dehydrogenase*** |
| FTL_0097 | hypothetical protein |
| FTL_0113 | *intracellular growth locus, subunit C* |
| FTL_0115 | *conserved hypothetical protein* |
| FTL_0116 | *conserved hypothetical protein* |
| FTL_0118 | *conserved hypothetical protein* |
| FTL_0119 | *conserved hypothetical protein* |
| FTL_0120 | *conserved hypothetical protein* |
| FTL_0121 | *conserved hypothetical protein* |
| FTL_0122 | *conserved hypothetical protein.* |
| FTL_0123 | *conserved hypothetical protein* |
| FTL_0124 | *hypothetical protein* |
| FTL_0125 | *conserved hypothetical protein* |
| FTL_0126 | *conserved hypothetical protein* |
| FTL_0129 | *2-isopropylmalate synthase* |
| FTL_0130 | isopropylmalate/homocitrate/citramalate synthase family protein |
| FTL_0131 | Branched-chain amino acid aminotransferase protein (class IV) |
| FTL_0147 | hypothetical protein |
| FTL_0207 | Pyrrolidone-carboxylate peptidase |
| FTL_0208 | hypothetical membrane protein |
| FTL_0209 | DNA polymerase III (CHI subunit) protein |
| FTL_0221 | amino acid permease |
| FTL_0425 | Type IV pili glycosylation protein |
| FTL_0449 | hypothetical protein |
| FTL_0491 | outer membrane lipoprotein |
| FTL_0499 | S-adenosylmethionine decarboxylase *** |
| FTL_0570 | hypothetical protein |
| FTL_0673 | Pantoate-beta-alanine ligase*** |
| FTL_0674 | 3-methyl-2-oxobutanoate hydroxymethyltransferase*** |
| FTL_0753 | Aminoacylase |
| FTL_0767 | conserved hypothetical protein bifunctional 4'-phosphopantothenoylcysteine |
| FTL_0808 | decarboxylase,phosphopantothenoylcysteine synthetase |
| FTL_0810 | cation transport regulator |
| FTL_0814 | conserved hypothetical protein |
| FTL_0879 | beta-lactamase |
| FTL_0924 | proton-dependent oligopeptide transporter |
| FTL_0942 | nicotinamide mononucleotide transport (NMT) family protein |
| FTL_1174 | cystathionine beta-synthase (cystein synthase) |
| FTL_1213 | hypothetical protein |
| FTL_1219 | Aminotransferase, class II |
| FTL_1225 | conserved hypothetical protein |
| FTL_1242 | ThiJ/PfpI family protein |
| FTL_1243 | conserved hypothetical protein |
| FTL_1509 | D-alanyl-D-alanine carboxypeptidase/D-alanyl-D-alanine-endopeptidase |
| FTL_1545 | SNO glutamine amidotransferase family protein |
| FTL_1546 | Pyridoxine/pyridoxal 5-phosphate biosynthesis protein |
| FTL_1678 | conserved membrane hypothetical protein |
| FTL_1790 | major facilitator superfamily (MFS) transport protein |
| FTL_1901 | conserved hypothetical membrane protein |

Figure 6:
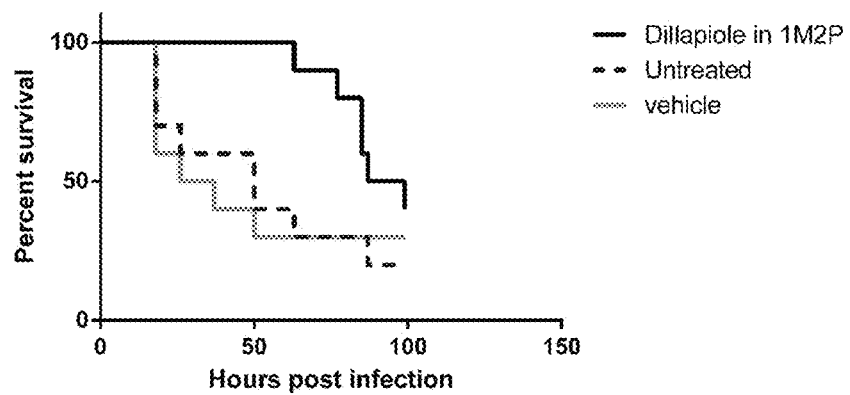
FIG. 6 is a graph showing wax worms infected with *A. baumannii* exhibit increased survival when treated with dillapiole.

To determine whether dillapiole treatment also diminished the virulence of other pathogenic microorganisms, wax worm larvae (*Galleria mellonella*) were infected with *Acinetobacter baumannii* and treated with dillapiole or a vehicle. Waxworms treated with the dillapiole exhibited a significantly higher rate of survival compared to those treated with the vehicle control (FIG. 6). Importantly, dillapiole did not diminish *A. baumannii* viability in rich growth media (data not shown), which is consistent with the *F. tularensis* data indicating that this compound functions by dampening bacterial pathogenesis.

Figure 7A:
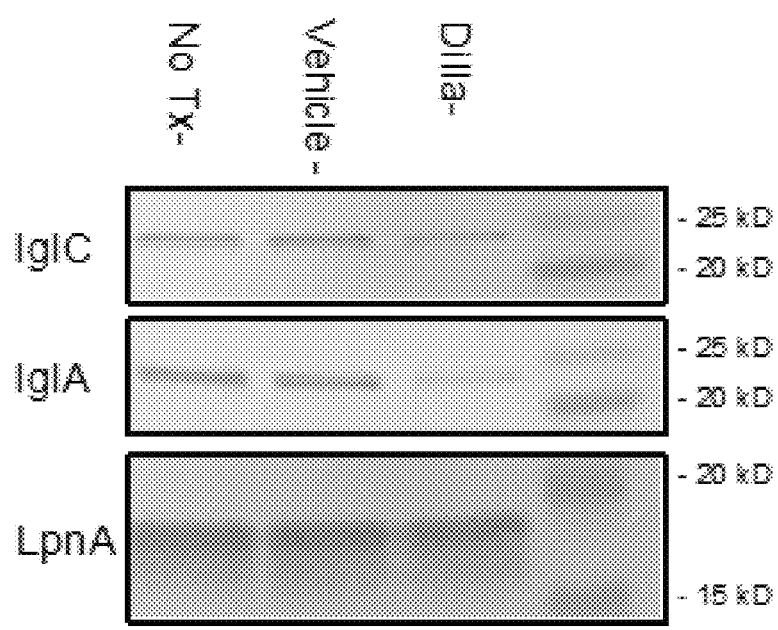
FIGS. 7A-7B includes images and graphs showing dillapiole treatment reduces intracellular growth locus protein A (IglA) and intracellular growth locus protein C (IglC) protein expression in *F. tularensis* LVS, where *F. tularensis* LVS bacteria were cultured with dillapiole (20 μg/ml), vehicle, or were untreated, where cell lysates from stationary phase cultures were subjected to SDS-PAGE and the separated proteins were transblotted to nitrocellulose, where the nitrocellulose was blocked and then probed with either anti-IglA, anti-IglC, or anti-LpnA antibodies (BEI resources) and where, after washing, a secondary antibody that was conjugated to alkaline phosphatase was used for detection (see FIG. 7A), with digital images of the blots analyzed using ImageJ, and data generated from 3-4 independent replicate blots analyzed using a paired t test (% no treatment protein expression of vehicle or dillapiole treated bacteria; for dillapiole vs. vehicle: IglC, $P=0.0305$; IglA, $P=0.0040$; for LpnA, $P=0.7157$).
Figure 7B:
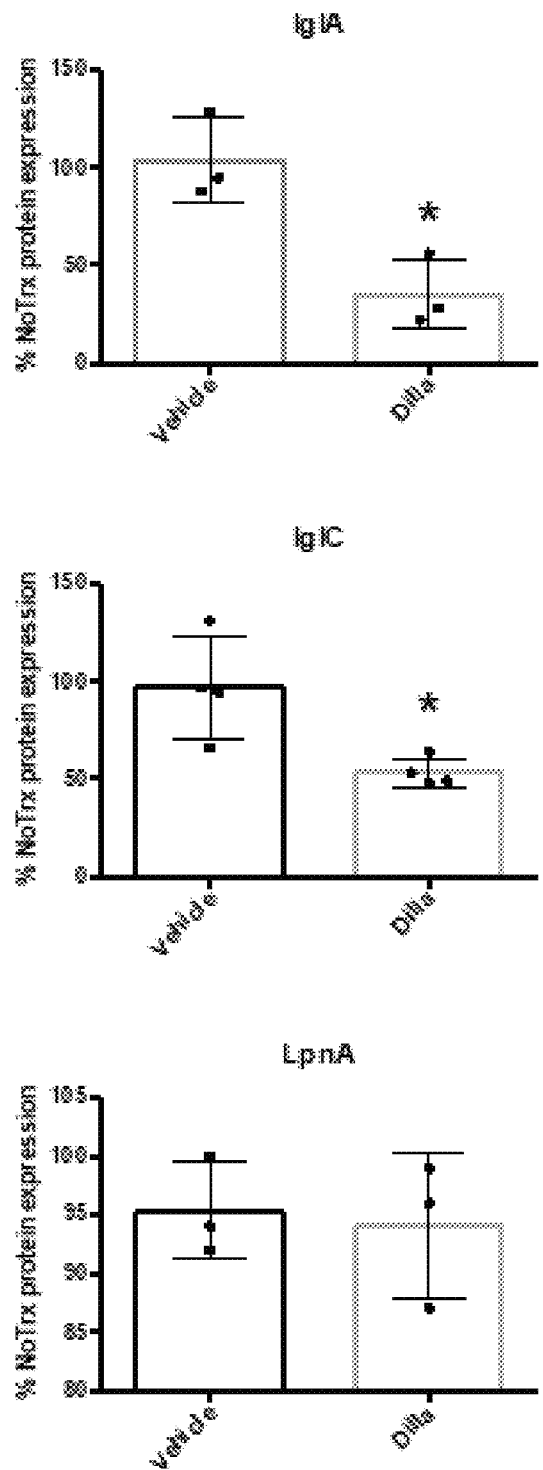

To determine whether or not the decrease in FPI transcription led to a reduction in protein level, Western blotting of *F. tularensis* LVS cell lysates from cultures that had been treated with dillapiole (20 µg/ml) or vehicle was conducted (FIG. 7). The lysates were subjected to SDS-PAGE and then transferred to nitrocellulose paper. After blocking, the nitrocellulose was probed with anti-IglA, anti-IglC (two FPI proteins), or anti-LpnA (encoded by a gene whose transcription was unaffected by dillapiole). The Western blotting showed a significant reduction of IglA and IglC from bacteria cultivated in the presence of dillapiole (FIGS. 7A-7B). However, LpnA production was unaffected by the presence of dillapiole (FIGS. 7A-7B)—a result consistent with the RNA-seq data. Notably, the presence of dillapiole did not affect bacterial growth as determined by optical density (data not shown). Altogether, these results indicate that dillapiole reduces expression of key virulence factors of *F. tularensis* and indicate that this compound reduces bacterial pathogenesis during infection.

In summary, dillapiole is a novel antibacterial therapeutic that exerts its activity through dampening virulence factor expression of pathogenic bacteria. This treatment paradigm is different than that of existing antibiotics and therefore minimizes the selection for antibiotic resistance. This is because traditional antibiotics target central biological processes that are required for normal viability and growth of the bacteria (even outside the context of infection) while dillapiole only affects expression of genes required for pathogenesis and does not affect bacterial viability. Therefore, dillapiole does not exert the degree of selective pressure compared to traditional antibiotics which will likely minimize the development of resistance to this novel treatment.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

Boletín Latinoamericano y del Caribe de Plantas Medicinales y Aromáticas 13 (6): 517-526.

Br. J. Med. Med. Res. 2016, 15, 1-10.

Pharmaceutical Biology, 2011; 49(11): 1173-1179.

J Bacteriol. 2004 October; 186(19):6430-6.

Infect Immun. 2010 June; 78(6):2607-19.

Mol Microbiol. 1998 July; 29(1):247-59.

Infect Immun. 2006 December; 74(12):6642-55.

PLoS Pathog. 2007 June; 3(6):e84.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method for treating a bacterial infection, comprising administering to a subject in need thereof an effective amount of dillapiole, wherein the bacterial infection is a *F. tularensis* or an *A. baumannii* infection, and wherein the dillapiole or the derivative thereof has the formula:

wherein $R_1$ and $R_2$ are independently selected from a hydrogen atom and an alkyl group; or wherein $R_1$ is selected from a propene group, a propyne group, a propane group, an isopropyl group, or a cyclopropyl group.

2. The method of claim 1, wherein administering the dillapiole comprises administering an amount of dillapiole sufficient to reduce an amount of expression of one or more virulence factors in a bacterium, to reduce an amount of activity of MglA/SspA in the bacterium, or to reduce an amount of replication by the bacterium.

3. The method of claim 2, wherein the replication is intracellular replication.

4. The method of claim 2, wherein the bacterium is an antibiotic resistant bacterium.

5. The method of claim 1, wherein administering the dillapiole comprises administering an amount of dillapiole sufficient to reduce an expression level of tumor necrosis factor alpha (TNFα) in the subject.

6. A method for reducing bacterial virulence, comprising contacting a bacterium with an effective amount of dillapiole, wherein the bacterium is a bacterium reliant on activity of MglA/SspA for pathogenesis, and wherein contacting the bacterium with the dillapiole comprises contacting the bacterium with an amount of the dillapiole sufficient to reduce an amount of activity of MglA/SspA in the bacterium or to reduce an expression level of one or more genes controlled by MglA/SspA in the bacterium, and wherein the dillapiole has the formula:

wherein R₁ and R₂ are independently selected from a hydrogen atom and an alkyl group; or

[chemical structure: methylenedioxybenzene with two methoxy groups and R₁ substituent]

wherein R₁ is selected from a propene group, a propyne group, a propane group, an isopropyl group, or a cyclopropyl group.

7. The method of claim 6, wherein the one or more genes are encoded by the *Francisella* pathogenicity island (FPI).

8. The method of claim 6, wherein the bacterium is an antibiotic resistant bacterium.

9. The method of claim 6, wherein the bacterium is selected from *F. tularensis* or *A. baumannii*.

10. The method of claim 1, wherein administering the effective amount of dillapiole comprises administering dillapiole having the formula:

[chemical structure: dillapiole]

11. The method of claim 6, wherein administering the effective amount of dillapiole comprises administering dillapiole having the formula:

[chemical structure: dillapiole]

* * * * *

UNITED STATES PATENT AND TRADEMARK OFFICE
CERTIFICATE OF CORRECTION

| | |
|---|---|
| PATENT NO. | : 12,109,187 B2 |
| APPLICATION NO. | : 17/396223 |
| DATED | : October 8, 2024 |
| INVENTOR(S) | : Joseph A. Horzempa et al. |

It is certified that error appears in the above-identified patent and that said Letters Patent is hereby corrected as shown below:

In the Claims

Claim 1, Column 19, Line 67, delete "or the derivative thereof"

Signed and Sealed this
Twelfth Day of November, 2024

Katherine Kelly Vidal
*Director of the United States Patent and Trademark Office*